United States Patent
Cheong et al.

(10) Patent No.: US 10,787,692 B2
(45) Date of Patent: *Sep. 29, 2020

(54) L-THREONINE AND L-TRYPTOPHAN PRODUCING BACTERIA STRAIN AND METHOD OF MAKING SAME

(71) Applicant: CJ Cheiljedang Corporation, Seoul (KR)

(72) Inventors: Ki Yong Cheong, Gyeonggi-do (KR); Seok Myung Lee, Seoul (KR); Young Bin Hwang, Seoul (KR); Keun Cheol Lee, Gyeonggi-do (KR); Kwang Ho Lee, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/465,881

(22) Filed: Mar. 22, 2017

(65) Prior Publication Data

US 2017/0198317 A1    Jul. 13, 2017

Related U.S. Application Data (63) Continuation of application No. 14/370,500, filed as application No. PCT/KR2013/000072 on Jan. 7, 2013, now Pat. No. 10,041,099.

(30) Foreign Application Priority Data

Jan. 6, 2012   (KR) .................. 10-2012-0001819

(51) Int. Cl.
C12P 13/22 (2006.01)
C12N 9/02 (2006.01)
C07K 14/245 (2006.01)
C12P 13/08 (2006.01)
C12N 1/20 (2006.01)

(52) U.S. Cl.
CPC .......... *C12P 13/227* (2013.01); *C07K 14/245* (2013.01); *C12N 1/20* (2013.01); *C12N 9/0053* (2013.01); *C12N 9/0071* (2013.01); *C12P 13/08* (2013.01); *C12Y 114/11* (2013.01); *Y02P 20/59* (2015.11)

(58) Field of Classification Search
None
See application file for complete search history.

(56) References Cited

U.S. PATENT DOCUMENTS

2007/0054358 A1   3/2007   Blattner et al.
2015/0050703 A1   2/2015   Cheong et al.

FOREIGN PATENT DOCUMENTS

| KR | 10-2005-0079343 A | 8/2005 |
| KR | 10-2008-0054481 A | 6/2008 |
| KR | 10-2009-0076389 A | 7/2009 |
| KR | 10-2010-0099571 A | 9/2010 |
| WO | WO 2002/099086 | 12/2002 |
| WO | WO 2005/075626 A1 | 8/2005 |
| WO | WO 2008/072891 A1 | 6/2008 |

OTHER PUBLICATIONS

Chassagnole et al. (2001) Biochem. J., vol. 356, pp. 433-444, "Control of the threonine-synthesis pathway in *Escherichia coli*: a theoretical and experimental approach".
Blaesen et al. (2007) J. Biotechnol. vol. 132, No. 4, pp. 431-437, "Recycling of bacterial biomass in a process of L-threonine production by means of a recombinant strain of *Escherichia coli*".
EP Supplemental Search Report issued in EP 13733718, dated Aug. 6, 2015.
Hara et al. (2009) Metabolic Engineering 11(1):1-7, "Systematic genome-wide scanning for genes involved in ATP generation in *Escherichia coli*".
Hara et al. (Aug. 2009) FEMS Microbiology Letters, 297(2):217-224, "Glutathione production by efficient ATP-regenerating *Escherichia coli* mutants".
International Search Report issued in PCT/KR2013/000072, dated May 31, 2013.
Nizam et al. (2009) Biochemical Engineering Journal, vol. 44, No. 2-3, pp. 240-250, "Effects of arcA and arcB genes knockout on the metabolism in *Escherichia coli* under aerobic condition".
Shimada et al. (1989) J. Ferment. Bioeng.vol. 67, No. 3, pp. 215-218, "Application of Powdered Ceramics Support to the Production of L-Tryptophan by Resting *Escherichia coli* K-12 Cells".
Wells, James A. (Sep. 18, 1990) Biochemistry 29(37):8509-8517, "Additivity of Mutational Effects in Proteins".
NCBI, Genbank PKHD-type hydroxylase YbiX [*Escherichia coli* H591] Gen bank; EGI46527.1, Jul. 25, 2016.

*Primary Examiner* — Hope A Robinson
(74) *Attorney, Agent, or Firm* — Adsero IP (57) ABSTRACT

The present invention relates to a microorganism able to produce L-threonine or L-tryptophan, and to a method for producing L-threonine or L-tryptophan by using same. More specifically, the present invention relates to: recombinant *Escherichia coli* which is more efficient in producing L-threonine or L-tryptophan by increasing the ability to produce ATP which is used as the most plentiful energy source in cells when producing L-threonine or L-tryptophan; and a method for producing L-threonine or L-tryptophan by using same.

7 Claims, 2 Drawing Sheets

Specification includes a Sequence Listing.

L-THREONINE AND L-TRYPTOPHAN PRODUCING BACTERIA STRAIN AND METHOD OF MAKING SAME

RELATED APPLICATIONS

This application is a continuation of U.S. Pat. No. 10,041,099 filed Jul. 3, 2014, entitled "Microorganism able to Produce L-Amino Acid, and Method for Producing L-Amino Acid by Using the Same". U.S. Pat. No. 10,041,099 is a National Stage Entry of International Application No. PCT/KR2013/000072, filed on Jan. 7, 2013, and claims the benefit of Korean Application No. 10-2012-0001819, filed on Jan. 6, 2012. Each of the applications referenced above are hereby incorporated by reference in their entirety for all purposes as if fully set forth herein.

TECHNICAL FIELD

The present invention relates to a microorganism able to produce L-threonine or L-tryptophan and to a method of producing L-threonine or L-tryptophan using the same.

Incorporated by reference herein in its entirety is the Sequence Listing entitled "sequence Listing.txt", created Mar. 21, 2017, size of 11 kilobytes.

BACKGROUND ART

It is known that microorganisms which produce useful products through fermentation require very large amounts of energy such as ATP when the biosynthetic pathway is enhanced.

As is known in the art, it is very important that the intracellular balance between nicotinamide adenine dinucleotide (NAD(H)) that is produced by catabolic reactions and nicotinamide adenine dinucleotide phosphate NADP(H) that is used in anabolic reactions in microbial metabolic processes. NAD(H) is an intermediate in the catabolic reactions that generate ATP through the oxidation of food and functions as an energy source. And NADP(H) play roles in providing a reducing power in the in vivo metabolic process, that is providing the high-energy electrons needed to synthesize molecules by reacting with enzyme which generally catalyze an anabolic reactions. The balance therebetween is regulated either by the phosphorylation of NAD as shown in the following equation 1) or by the dephosphorylation of NADP as shown in the following equation 2).

$$NAD^+ + ATP \Leftrightarrow NADP^+ + ADP \qquad \text{Equation 1)}$$

$$NADP^+ \Leftrightarrow NAD^+ + phosphate \qquad \text{Equation 2)}$$

Thus, in order to effectively produce reducing power such as NADPH, a phosphate source such as ATP should be increased together.

ATP (Adenosine-5'-triphosphate) has a high energy phosphate bond, and generates energy when it is hydrolyzed to ADP and phosphate. ATP is produced mainly by chemiosmotic phosphorylation via the electron transport system in microorganisms or by substrate-level phosphorylation. The produced ATP is degraded to supply the energy required for cells and is reused by regenerating via glycolysis pathway or oxidative phosphorylation.

Based on this fact, studies have been conducted to apply bacteria's ATP energy regenerating process to the mass production of useful products in order to facilitate energy supply (Biosci Biotechnol Biochem., (1997) 61: 840-845). In studies on the regeneration of ATP in *E. coli*, it was found that the level of ATP in a microorganism is about 150% higher than that in the parent strain when a few genes, including ysaA (NCBI Gene ID: 948085), ydaS (NCBI Gene ID: 945923) and ybiX (NCBI Gene ID: 947502) genes was deficient, respectively, and this finding was applied to the production of glutathione (FEMS Microbiol Lett., (2009) 297:217-224). However, there was no direct report directly explains the increase in production of amino acids caused by attenuation in the activities of proteins that are encoded by the genes.

DISCLOSURE

Technical Problem

The present inventors have found that increasing the intracellular level of ATP, which is used as the most plentiful energy source in cells producing L-amino acid, is effective to increase the production of L-threonine or L-tryptophan, thereby completing the present invention.

An object of the present invention is to provide a recombinant *E. coli* strain which has an increased L-threonine or L-tryptophan productivity by increasing the productivity of ATP.

Another object of the present invention is to provide a method of producing L-threonine or L-tryptophan using the recombinant *E. coli* strain.

Technical Solution

In order to accomplish the above objects, an embodiment of the present invention provides an L-threonine or L-tryptophan producing recombinant *E. coli* strain, wherein the strain is modified to attenuate(weaken) activity of at least one protein selected from the group consisting of a protein YsaA having an amino acid sequence represented by SEQ ID NO: 2, a protein YdaS having an amino acid sequence represented by SEQ ID NO: 4, and a protein YbiX having an amino acid sequence represented by SEQ ID NO: 6.

An embodiment of The present invention also provides a method for producing L-threonine or L-tryptophan, which comprises culturing the recombinant *E. coli* strain.

Advantageous Effects

The present invention provides a recombinant microorganism whose L-threonine or L-tryptophan productivity is improved by increasing the intracellular ATP level in a microorganism having L-threonine or L-tryptophan productivity. According to the present invention, it provides a method to enhance production of L-threonine or L-tryptophan by recovering the balance of energy metabolism to increase the cellular activity and reduce the culture time.

BEST MODE

Hereinafter, the present invention will be described in detail.

An embodiment of the present invention provides an L-threonine or L-tryptophan producing recombinant *E. coli* strain, wherein the strain is modified to attenuate activity of at least one selected from the group consisting of a protein YsaA having an amino acid sequence represented by SEQ ID NO: 2, a protein YdaS having an amino acid sequence represented by SEQ ID NO: 4, and a protein YbiX having an amino acid sequence represented by SEQ ID NO: 6.

An L-threonine or L-tryptophan producing microorganism that may be used in the present invention may be any microorganism capable of producing L-threonine or L-tryptophan, such as *Escherichia* sp. Bacterium, *E. coli, Coryneform bacterium, Serratia* sp. bacterium, *Providencia* sp. bacterium, or the like. Specifically, a microorganism belonging to the genus *Escherichia* may be used.

In a specific embodiment of the present invention, recombinant *E. coli* strain CJ600 (KCCM 10812P) (Korean Patent Registration No. 10-0792095) having L-tryptophan productivity is used, which is obtained by genetically engineering an recombinant *E. coli* strain (KFCC 10066) having L-phenylalanine productivity so as to desensitize the tryptophan auxotrophy, block L-phenylalanine biosynthesis and enhance tryptophan biosynthesis-related genes.

In another specific embodiment of the present invention, recombinant *E. coli* strain FTR2533 (KCCM-10541) (Korean Patent Registration No. 10-0576342) having L-threonine productivity is used, which is obtained by genetically engineering an *E. coli* mutant strain (KFCC 10718) having L-threonine productivity so as to inactivate the wild-type galR gene.

YsaA, a protein having an amino acid sequence represented by SEQ ID NO: 2, is predicted a hydrogenase of 4Fe-4S ferredoxin-type component, but its exact function has not yet been found.

YdaS, a protein having an amino acid sequence represented by SEQ ID NO: 4, is predicted a DNA binding transcription regulator, but its exact function has not yet been found.

YbiX, a protein having an amino acid sequence represented by SEQ ID NO: 6, is one of the Fe(II)-dependent oxygenase superfamily, which functions as an oxidoreductase that oxidizes its substrate using oxygen.

The polypeptides YsaA, YdaS and YbiX of the present invention have the amino acid sequences represented by SEQ ID NOS: 2, 4 and 6, respectively, but are not limited thereto, because the amino acid sequences of the proteins may be depending on the species or strains of microorganisms.

In other words, the proteins of the present invention may be mutants or artificial variants encoding a protein that has an amino acid sequence including a substitution, deletion, insertion, addition or inversion of one or several amino acids in one or more positions of the amino acid sequence represented by SEQ ID NO: 2, 4 or 6, as long as the mutants or artificial variants can be helpful in increasing the production of amino acid by attenuating the activities described in the present invention. Herein, the number of "several" amino acids differs depending on the position or type of amino acid residues in the three-dimensional structure of the protein, but is particularly 2-20, specifically 2-10, and more specifically 2-5. In addition, this substitution, deletion, insertion, addition or inversion of amino acids also include those alterations caused by a naturally occurring mutation or artificial variation based on the difference in individuals or species of microorganisms having the activity of the polypeptides.

As used herein, the term "attenuation" means that the activity of a protein is weakened either by deleting part or all of the gene encoding the protein, or by modifying an expression regulatory sequence to reduce the expression of the gene, or by modifying the chromosomal gene sequence to weaken the activity of the protein, or by combinations thereof.

In the present invention, attenuation of the activity may be achieved by a method selected from the group consisting of: 1) deleting part or all of a polynucleotide encoding the protein; 2) modifying an expression regulatory sequence to reduce the expression of the polynucleotide; 3) modifying the chromosomal polynucleotide sequence to weaken the activity of the protein; and 4) combinations thereof.

The method for deletion of part or all of the polynucleotide encoding the protein may be performed by replacing a polynucleotide which encodes an endogenous target protein in the chromosome, with either a polynucleotide that a part of nucleic acid sequence is deleted or a marker gene through chromosome insertion vector.

Herein, the term "a part of" nucleic acid sequence differ depending on the kind of gene, but is regardless of the position thereof, and it is specifically 1-200, mor specifically 1-100, and even more specifically 1-50.

Also, the method of modifying the expression regulatory sequence to reduce the expression of the polynucleotide may be performed either by inducing a mutation in the expression regulatory sequence by the deletion, insertion, non-conservative or conservative substitution, or combinations thereof, of one or more nucleotides to attenuate the activity of the expression regulatory sequence, or by replacing the expression regulatory sequence with weaker activity. The expression regulatory sequence includes a promoter, an operator sequence, a sequence encoding a ribosome-binding site, a sequence regulating the termination of transcription and translation.

In addition, the method of modifying the chromosomal polynucleotide sequence encoding the protein of the present invention may be performed either by inducing a mutation in the sequence by the deletion, insertion, non-conservative or conservative substitution, or combinations thereof, of one or more nucleotides to attenuate the activity of the sequence, or by replacing the sequence with an modified nucleotide sequence having weaker activity.

The polynucleotide encoding the protein of the present invention can be introduced into a host cell and may be substituted with a codon difficult to express in the host. In addition, the N-terminus or C-terminus thereof may be extended or deleted, and the start codon may be modified to regulate the expression level.

Each of the polynucleotides of the present invention may have a polynucleotide sequence encoding a protein having a homology of at least 80%, specifically at least 90%, more specifically at least 95%, and even more specifically at least 97% to the amino acid sequence of each represented by SEQ ID NOS: 2, 4 and 6, as long as the polynucleotide can attenuate the protein activity of the variant. More specifically, the polynucleotides have a polynucleotide sequence represented by SEQ ID NOs: 1, 3 and 5, respectively.

As used herein, the term "homology" refers to the identity between two amino acid sequences. The homology can be determined using well-known methods, for example, the computer program BLAST 2.0 which calculates parameters like as score, identity, and similarity.

Also, the polynucleotide sequences of the present invention may be hybridized with the polynucleotide sequences represented by SEQ ID NOS: 1, 3 and 5 and probes produced from the above-described nucleotide sequences under stringent conditions, and may be modified sequences encoding normally functioning proteins.

As used herein, the term "stringent conditions" refers to conditions that allow specific hybridization between polynucleotides. Alternatively, the term is related to polypeptides or proteins, including derivatives thereof (Molecular Cloning, A Laboratory Manual, J. Sambrook et al., Editors, 2nd Edition, Cold Spring Harbor Laboratory press, Cold Spring Harbor, N.Y., 1989; or Current Protocols in Molecular Biology, F. M. Ausubel et al., Editors, John Wiley & Sons, Inc., New York).

Specifically, the "stringent conditions" refer to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate at pH 7. After hybridization, the membrane to which the DNA has been transferred is washed in 2×SSC at room temperature and then in 0.1-0.5×SSC/0.1×SDS at 68° C.

As used herein, the term "vector" refers to a DNA construct containing the nucleotide sequence of a target protein-encoding gene operably linked to a suitable regulatory sequence so as to be able to express the target gene in a suitable host cell. The regulatory sequence includes a promoter capable of initiating transcription, any operator for regulating this transcription, a sequence encoding a suitable mRNA ribosome binding site, and a sequence for regulating the termination of transcription and translation. Once transformed into a suitable host, the vector may replicate or function independently of the host genome, or may, in some cases, integrate into the genome itself.

The vector that is used in the present invention is not specifically limited and may be any vector known in the art, as long as it can replicate in a host. Examples of the commonly used vectors may include natural or recombinant plasmids, cosmids, viruses, and bacteriophages. For example, the phage vector or cosmid vectors include pWE15, M13, λBL3, λBL4, λXII, λSHII, λPII, λ10, λ11, Charon4A, and Charon21A, and the plasmid vectors include pBR, pUC, pBluescriptII, pGEM, pTZ, pCL1920 and pET-type plasmids. Vectors that may be used are not particularly limited, and any known expression vectors may be used. Specifically, pACYC177, pACYC184, pCL1920, pECCG117, pUC19, pBR322, pMW118 or pCC1BAC vectors may be used. Most specifically, pACYC177, pCL1920 and pCC1BAC vectors may be used.

Further, the vector that is used in the present invention is a vector capable of transforming host cells, to insert the polynucleotide encoding the target protein into the chromosome of the host cell. Specific examples of the vector include, but are not limited to, the shuttle vector pECCG112 that can self-replicate in both directions in *E. coli* and Coryne-type bacteria (Kap-Soo, Noh, Kor. Jour. Microbiol. July 1991, p149-154).

Also, the polynucleotide encoding the endogenous target protein in the chromosome can be replaced with a new polynucleotide by a vector for insertion into the bacterial chromosome. Insertion of the polynucleotide into the chromosome can be performed by any method known in the art, for example, homologous recombination. Because the vector of the present invention can be inserted into the chromosome by homologous recombination, it may further comprise a selection marker for confirming its insertion into the chromosome. The selection marker is used to select a cell transformed with the vector, that is, confirm the insertion of the target polynucleotide. The selection marker that is used in the present invention may be selected from markers that provide selectable phenotypes, such as drug resistance, auxotrophy, resistance to cytotoxic agents, or surface protein expression. Only cells expressing the selection marker are able to survive or to show different phenotypes under the environment treated with the selective agent, and thus the transformed cells can be selected.

As used herein, the term "transformation" means introducing a vector comprising the polynucleotide encoding the target protein into a host cell so as to be able to express the protein encoded by the polynucleotide in the host cell. The transformed polynucleotides include all the genes inserted in the chromosome of the host cell or located outside the chromosome, as long as they can be expressed in the host cell. In addition, the polynucleotides include DNA and RNA, which encode the target protein. As long as the polynucleotide can be introduced in the host cell and expressed therein, the gene may be introduced in any form. For example, the polynucleotide can be introduced into the host cell in the form of an expression cassette which is a polynucleotide construct including all elements for expressing the gene. The expression cassette includes a promoter which is operably linked to the gene, a transcription termination signal, a ribosome binding site, and a translation termination signal. The expression cassette may be in the form of an expression vector capable of self-replicating. The polynucleotide may also be introduced into the host cell by itself, and be operably linked to the sequence necessary for expression in the host cell.

Specifically, attenuation of the activity of the protein that is encoded by the ysaA, ydaS or ybiX gene may be achieved by deletion of the gene. Specifically, a mutation in the gene can be induced using chemicals or light such as UV light, thereby obtaining a variant having the deleted gene.

Alternatively, a variant lacking the activity of the protein can be obtained by substituting the chromosomal gene to the nucleotide lacking the activity by a gene recombination technique, by a method of gene replacement through homologous recombination.

Also, an embodiment of the present invention also provides a method for producing L-threonine or L-tryptophan, the method comprising culturing an L-threonine or L-tryptophan producing recombinant *E. coli* strain, wherein the strain is modified to attenuate activity of at least one selected from the group consisting of a protein YsaA having an amino acid sequence represented by SEQ ID NO: 2, a protein YdaS having an amino acid sequence represented by SEQ ID NO: 4, and a protein YbiX having an amino acid sequence represented by SEQ ID NO: 6. The culture process of the present invention can be performed in suitable media and culture conditions known in the art. This culture process can be easily modified by any person skilled in the art depending on the type of strain selected. Examples of the culture process include, but are not limited to, batch culture, continuous culture, and fed-batch culture.

The media and culture conditions that are used in culture of the microorganism of the present invention may be those as long as that are used in culture of microorganisms belonging to the genus *Escherichia*, but these should properly satisfy the requirements of the microorganism of the present invention.

In a specific embodiment of the present invention, the microorganism may be cultured in a conventional medium containing suitable carbon sources, nitrogen sources, amino acids, vitamins and the like under aerobic conditions while adjusting temperature, pH and the like.

Carbon sources that may be used in the present invention include carbohydrates such as glucose, fructose, sucrose, maltose, mannitol, sorbitol; alcohols such as sugar alcohol, glycerol, pyruvic acid, lactic acid and citric acid; and amino acids such as organic acid, glutamic acid, methionine and lysine. In addition, natural organic nutrient sources such as starch hydrolysates, molasses, blackstrap molasses, rice bran, cassava, bagasse and corn steep liquor may be used. Specifically, the organic nutrient sources include glucose and sterile pretreated molasses (i.e., molasses converted to reduced sugars), and suitable amounts of carbon sources may be used without limitation.

Nitrogen sources that may be used in the present invention include inorganic nitrogen sources such as ammonia, ammonium sulfate, ammonium chloride, ammonium acetate, ammonium phosphate, ammonium carbonate, and ammonium nitrate; amino acids such as glutamic acid, methionine and glutamine; and organic nitrogen sources such as peptone, NZ-amine, meat extract, yeast extract, malt extract, corn steep liquor, casein hydrolysate, fish meal or its digested product, defatted soybean cake or its digested product, etc. These nitrogen sources may be used alone or in combination. The medium may contain potassium phosphate monobasic, potassium phosphate dibasic and corresponding sodium-containing salts, as phosphorus sources.

Inorganic compounds that may be used in the present invention include sodium chloride, calcium chloride, iron chloride, magnesium sulfate, iron sulfate, manganese sulfate and calcium carbonate. In addition, the medium may contain amino acids, vitamins and suitable precursors. These media or precursors may be added to the medium in a batch or continuous manner.

Compounds such as ammonium hydroxide, potassium hydroxide, ammonia, phosphoric acid and sulfuric acid may be added to the medium in a suitable manner during culture to adjust the pH of the culture medium.

In addition, during culture, a defoaming agent such as fatty acid polyglycol ester may be used to suppress the formation of bubbles. Further, in order to maintain the culture medium in an aerobic state, oxygen or oxygen-containing gas may be injected into the culture medium. In addition, in order to maintain the culture medium in an anaerobic or non-aerobic state, no gas is injected, or nitrogen, hydrogen or carbon dioxide gas may be injected into the culture medium. The culture medium is typically maintained at a temperature ranging from 27° C. to 37° C., and specifically from 30 r to 35° C. Culture of the microorganism can be continued until the desired level of the useful substance will be obtained. Specifically, the culture period is from 10 to 100 hours.

The method of the present invention may further comprise purifying or recovering the L-amino acid produced in the culture step. The purification or recovery process can be performed by purifying or recovering the desired L-amino acid from the culture medium using a suitable method selected depending on the method used for culture of the microorganism, for example, a batch, continuous or fed-batch culture method.

Hereinafter, the present invention will be described in further detail with reference to examples. It is to be understood, however, that these examples are for illustrative purposes and are not intended to limit the scope of the present invention.

EXAMPLES

Example 1: Construction of L-Threonine and L-Tryptophan Producing Strains Having Attenuated Activity of Protein that is Encoded by ysaA, ydaS or ybiX Gene In this Example, each of the ysaA, ydaS and ybiX gene in the L-tryptophan producing strain KCCM10812P (Korean Patent Registration No. 10-0792095) and the L-threonine producing strain KCCM10541 (Korean Patent Registration No. 10-0576342) was deleted by homologous recombination.

The L-tryptophan producing parent strain KCCM10812P is a strain derived from an $E.$ $coli$ variant KFCC 10066 having L-phenylalanine productivity. It is a recombinant $E.$ $coli$ strain having L-tryptophan productivity, characterized in that chromosomal tryptophan auxotrophy was desensitized, the pheA, trpR, mtr and tnaAB genes were attenuated and the aroG and trpE genes were modified.

Also, the L-threonine producing parent strain KCCM10541 is a strain derived from $E.$ $coli$ KFCC10718 (Korean Patent Laid-Open Publication No. 1992-0008365). It has resistance to L-methionine analogue, a methionine auxotroph phenotype, resistance to L-threonine analogue, a leaky isoleucine auxotroph phenotype, resistance to L-lysine analogue, and resistance to α-aminobutyric acid, and is capable of producing L-threonine.

The ysaA, ydaS and ybiX genes to be deleted have the polynucleotide sequences represented by SEQ ID NOS: 1, 3, and 5 respectively.

For this purpose, the one-step inactivation method (developed by Datsenko K A et al.) that is a mutagenesis technique using lambda red recombinase was used (Proc Natl Acad Sci USA., (2000) 97: 6640-6645). As a marker for confirming insertion into the genes, the chloramphenicol-resistant gene of pUCprmfmloxC was used (Korean Patent Laid-Open Publication No. 2009-0075549).

About 1200-bp gene fragments were amplified by polymerase chain reaction (hereinafter referred to as PCR) using pUCprmfmloxC as a template and a pair of primers 1 and 2, a pair of primers 7 and 8 and a pair of primers 13 and 14, which have a portion of each of the three genes and a portion of the chloramphenicol-resistant gene of pUCprmfmloxC. The PCR was performed for 30 cycles, each consisting of denaturation at 94° C. for 30 sec, annealing at 55° C. for 30 sec and extension at 72° C. for 1 min.

TABLE 1

| Primer No. | Sequence | SEQ ID NO |
|---|---|---|
| 1 | 5'-GTAGGGACGCGCTCTCTGGCACTCTGCTGTTTTAGTGCAAAGGAGTGATCAGGTGACACTATAGAACGCG-3' | 7 |
| 2 | 5'-GGCATAAACAAAGCGCACTGTTCCGGCGTTGAGAAACGCCGGAAAACGTTTAGTGGATCTGATGGGTACC-3' | 8 |

TABLE 1-continued

| Primer No. | Sequence | SEQ ID NO |
|---|---|---|
| 3 | 5'-GCTTTGGACAAGTGCCAAAACTTTAACATTTCCTTCGTTGGATCAAAGCAGTAGGGACGCGCTCTCTGGC-3' | 9 |
| 4 | 5'-ATTGAATTTGGAAGAATTTGTAGGCCGGATAAGGCGTTTACGCCGCATCTGGCATAAACAAAGCGCACTG-3' | 10 |
| 5 | 5'-GAGAGAAAAATCTCCTGAAA-3' | 11 |
| 6 | 5'-CCTACATGATTTCTGCAATA-3' | 12 |
| 7 | 5'-ATTGCGTTAGGCGTCGCCTAATATTTCTGTGTGTTTTTGGAGTTCATTCGAGGTGACACTATAGAACGCG-3' | 13 |
| 8 | 5'-ATTCGATGTGCTCATGCTTGATTTTCATGAATCATTTGCCTCTTGATGTTTAGTGGATCTGATGGGTACC-3' | 14 |
| 9 | 5'-TTACATTAGGCAATCCCTACCCTTACTGCATTAGGCACAGCCTATTGACAATTGCGTTAGGCGTCGCCTA-3' | 15 |
| 10 | 5'-ATTGGCTACCCATGCCTGCCCTTTTTCGGCTGCTAGGGCAAACAACACTGATTCGATGTGCTCATGCTTG-3' | 16 |
| 11 | 5'-TATAGAGCCTTTCTTAATCC-3' | 17 |
| 12 | 5'-CGCAGATATTCTTCAGTAAT-3' | 18 |
| 13 | 5'-CATTTCTGATTCAGATGTGGGGCGCAGGCCCCACTTTTTGGAGAAATTGTAGGTGACACTATAGAACGCG-3' | 19 |
| 14 | 5'-TGTACAGTTAAGTGTAGCTAATCCAGGGACGAACTCGGGCAGTTCAAGCATAGTGGATCTGATGGGTACC-3' | 20 |
| 15 | 5'-ACCGTTATCACCCGGGCGAGCCAAGAACCTTCTTGCTCACAGCCAATATGCATTTCTGATTCAGATGTGG-3' | 21 |
| 16 | 5'-GTCATCGTTAGCCCAACCGGATGCCATATCGACCTCCCCATATCAATACTTGTACAGTTAAGTGTAGCTA-3 | 22 |
| 17 | 5'-AAAGGTTCAGACGGCGCGGT-3' | 23 |
| 18 | 5'-TAAGCGCACGCCAGGAATGG-3' | 24 |

Also, the DNA fragments obtained by the PCR amplification were electrophoresed on 0.8% agarose gel, and then eluted and used as templates in secondary PCR. Secondary PCR was performed so that the 5' and 3' terminal regions of the primary DNA fragments had 20 pairs of complementary nucleotide bases. About 1300-bp gene fragments were amplified by PCR using the eluted primary PCR products as templates and a pair of primers 3 and 4, a pair of primers 9 and 10 and a pair of primers 15 and 16, which have include the 5' and 3' regions of the genes. The PCR was performed for 30 cycles, each consisting of denaturation at 94° C. for 30 sec, annealing at 55° C. for 30 sec and extension at 72° C. for 1 min. The DNA fragments obtained by the PCR amplification were electrophoresed on 0.8% agarose gel, and then eluted and used in recombination.

According to the method developed by Datsenko K A et al. (Proc Natl Acad Sci USA., (2000) 97:6640 6645), an E. coli strain transformed with a pKD46 were made competent, and then transformed with the 1300-bp gene fragments obtained by PCR. The resulting strains were selected on LB medium having resistance to chloramphenicol. PCR was performed using a pair of primers 5 and 6, a pair of primers 11 and 12 and a pair of primers 17 and 18, and the amplification products had sizes of 1450, 1530 and 1640 bp, respectively, and were confirmed that the genes were deleted.

pKD46 was removed from the primary recombinant strains having chloramphenicol resistance, and then a pJW168 vector was introduced into the strains, and the chloramphenicol marker gene was removed from the bacterial cells (Gene, (2000) 247,255-264). The resulting bacterial cells were about 400-bp, 500-bp and 600-bp amplification products obtained by a pair of primers 5 and 6, a pair of primers 11 and 12 and a pair of primers 17 and 18, and were confirmed that the desired gene deletion was achieved.

According to the above-described method, the L-threonine producing strains KCCM10541 ΔysaA, KCCM10541 ΔydaS and KCCM10541 ΔybiX were constructed. Also, the L-tryptophan producing strains KCCM10812P ΔysaA, KCCM10812P ΔydaS and KCCM10812P ΔybiX were constructed.

Example 2: Construction of Recombinant L-Threonine and L-Tryptophan Producing Strains Having Deletion of Two or More of ysaA, ydaS and ybiX Genes According to the method described in Example, recombinant strains having a deletion of two or more of the genes were constructed.

A pKD46 vector for using lambda red recombinase was introduced into the strains having a deletion of any one of the genes, and then the strains were made competent. Also, gene fragments amplified by PCR to include a portion of the three genes and the chloramphenicol-resistant gene of pUCprmfmloxC were transformed into different strains having a deletion of one of the genes. The resulting strains were screened on LB medium having chloramphenicol resistance, and deletion of a combination of the genes was confirmed by the use of the primer pairs described in Example 1.

According to the above-described method, the L-threonine producing strains KCCM10541 ΔysaA ΔydaS, KCCM10541 ΔydaS ΔybiX, KCCM10541 ΔybiX ΔysaA and KCCM10541 ΔysaA ΔydaS ΔybiX were constructed. Also, the L-tryptophan producing strains KCCM10812P ΔysaA ΔydaS, KCCM10812P ΔydaS ΔybiX, KCCM10812P ΔybiX ΔysaA and KCCM10812P ΔysaA ΔydaS ΔybiX were constructed.

Among the recombinant strains obtained as described above, KCCM10541 ΔysaA ΔydaS ΔybiX and KCCM10812P ΔysaA ΔydaS ΔybiX were named "*E. coli* CA03-4257P" and "*E. coli* CA04-2002", respectively, and deposited at the Korean Culture Center of Microorganisms (361-221, Hongje 1-dong, Seodaemun-gu, Seoul, Korea), an international depository authority, on Dec. 29, 2011 under the accession numbers KCCM11243P and KCCM11245P, respectively.

Example 3: Measurement of Levels of ATP in Constructed L-Threonine Producing Strains and L-Tryptophan Producing Strains In this Example, the levels of ATP in the strains constructed in Examples 1 and 2 were quantitatively measured.

For this purpose, the method developed by Kiyotaka Y. Hara et al., which uses luciferase, was used ("An Efficient Method for Quantitative determination of Cellular ATP Synthetic Activity", J Biom Scre, (2006) V11:No.3:PP310-17).

Figure 1:
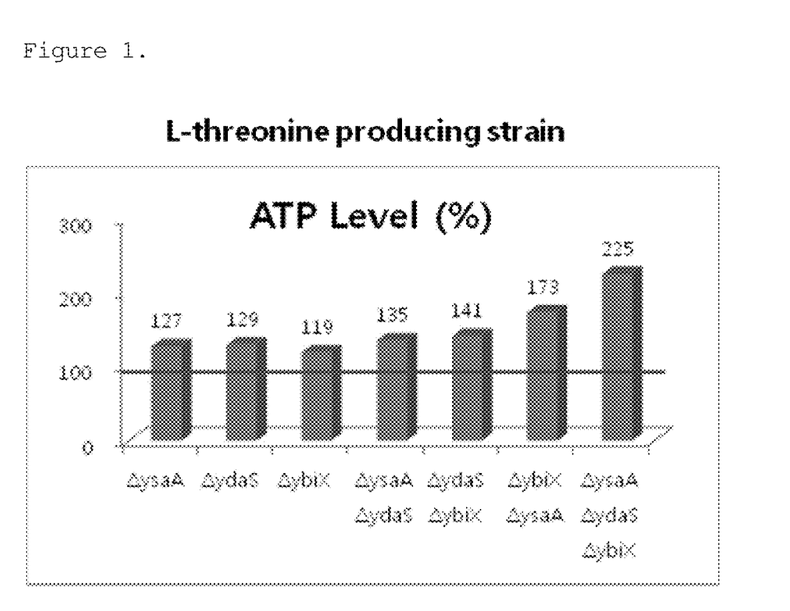
FIG. 1 shows the relative ATP level (%) of an L-threonine-producing strain relative to that of its parent strain.
Figure 2:
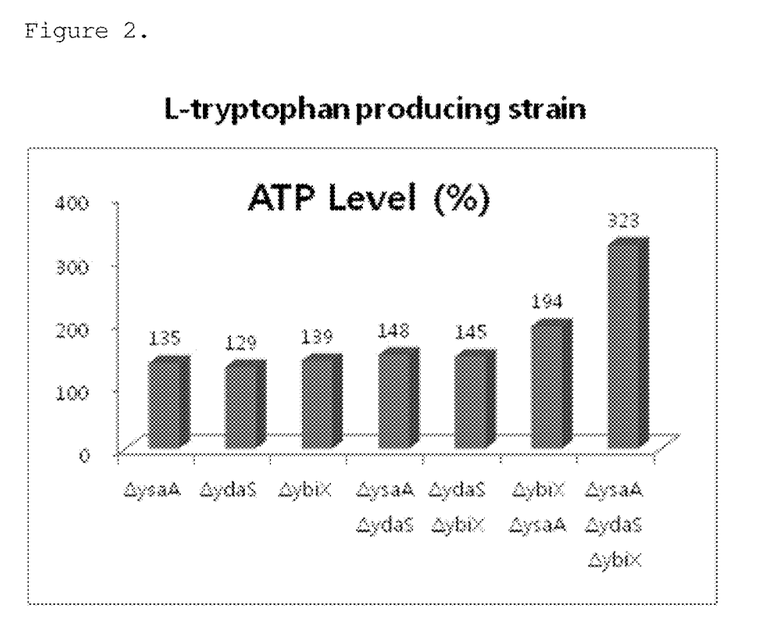
FIG. 2 shows the relative ATP level (%) of a L-tryptophan-producing strain relative to that of its parent strain.

Specifically, the strains having different genetic characters were cultured overnight in LB liquid medium containing glucose. The supernatant was removed by centrifugation, the bacterial cells were washed with 100 mM Tris-Cl (pH 7.5), and then treated with PB buffer (permeable buffer: 40%[v/v] glucose, 0.8%[v/v] Triton X-100™) for 30 minutes to release intracellular ATP. Next, the supernatant was removed by centrifugation, and luciferin as a substrate for luciferase was added to the cells. The cells were allowed to stand for 10 minutes, and then luciferase activity in the cells was measured with a luminometer to quantitatively determine the ATP level. The results of the measurement are shown in FIGS. 1 and 2. All the results were recorded as the average of three repeated experiments.

As can be seen in FIGS. 1 and 2, the levels of ATP in the strains constructed from the L-threonine producing strain and the L-tryptophan producing strain in Examples 1 and 2 all increased. In addition, the ATP level was higher in the strains having a deletion of a combination of the genes than in the strains having a deletion of one of the gene.

Example 4: Examination of Titer of L-Threonine Producing Strain, which has Attenuated Activity of Alone or a Combination of Enzymes that are Encoded by ysaA, ydaS and ybiX Gene, in Glucose-Containing Medium According to the methods described in Examples 1 and 2, alone or a combination of the ysaA, ydaS and ybiX genes was deleted from the L-threonine producing strain KCCM10541 (Korean Patent Registration No. 10-0576342) to increase the intracellular ATP level. The titers of the resulting strains were evaluated using glucose as a carbon source.

Specifically, the strains having different genetic characters were cultured overnight on LB solid medium in an incubator at 33° C. and inoculated by a platinum loop into 25 mL of glucose-containing medium having the composition shown in Table 2 below. Then, the strains were incubated in an incubator at 33° C. and at 200 rpm for 50 hours. The results are shown in Table 3 below. All the results were recorded as the average of three flask results.

TABLE 2

| Composition | Concentration (per liter) |
|---|---|
| Glucose | 70 g |
| $KH_2PO_4$ | 2 g |
| $(NH_4)_2SO_4$ | 25 g |
| $MgSO_4 \cdot H_2O$ | 1 g |
| $FeSO_4 \cdot H_2O$ | 5 mg |
| $MnSO_4 \cdot H_2O$ | 5 mg |
| Yeast extract | 2 g |
| Calcium carbonate | 30 g |
| pH | 6.8 |

TABLE 3

| Strain | OD | Glucose consumption (g/L)* | L-threonine (g/L)** |
|---|---|---|---|
| KCCM10541 | 23.7 | 30.3 | 31.8 |
| KCCM10541 ΔysaA | 24.6 | 33.4 | 32.2 |
| KCCM10541 ΔydaS | 23.5 | 34.7 | 33.0 |
| KCCM10541 ΔybiX | 22.7 | 33.9 | 32.7 |
| KCCM10541 ΔysaA ΔydaS | 24.9 | 35.1 | 32.9 |
| KCCM10541 ΔydsS ΔybiX | 24.5 | 36 | 33.1 |
| KCCM10541 ΔybiX ΔysaA | 25.0 | 32.1 | 33.0 |
| KCCM10541 ΔysaA ΔydaS ΔybiX | 26.1 | 36.9 | 33.9 |

*measured at 30 hours
**measured at 50 hours

As can be seen in Table 3 above, we have demonstrated that the glucose utilization of the recombinant L-threonine producing *E. coli* strains constructed according to the present invention increased by up to about 22% compared to that of the parent strain, and the production of threonine of the recombinant strains increased by up to about 7% compared to that in the parent strain. In view of the ATP level shown in FIG. 1, these results indicate that the glucose consumption rate or amino acid productivity of the recombinant strains was increased by the increased ATP level.

Example 5: Examination of Titer of L-Threonine Producing Strain, which has Attenuated Activity of Alolne or a Combination of Enzymes that are Encoded by ysaA, ydaS and ybiX Gene, in Sucrose-Containing Medium According to the methods described in Examples 1 and 2, alone or a combination of the ysaA, ydaS and ybiX genes was deleted from the L-threonine producing strain KCCM10541 (Korean Patent Registration No. 10-0576342) to increase the intracellular ATP level. The titers of the resulting strains were evaluated using sucrose as a carbon source.

Specifically, the strains having different genetic characters were cultured overnight on LB solid medium in an incubator at 33° C. and inoculated by a platinum loop into 25 mL of sucrose-containing medium having the composition shown in Table 4 below. Then, the strains were incubated in an incubator at 33 t and at 200 rpm for 48 hours. The results are shown in Table 5 below. All the results were recorded as the average of three flask results.

TABLE 4

| Composition | Concentration (per liter) |
|---|---|
| Sucrose | 70 g |
| $KH_2PO_4$ | 2 g |
| $(NH_4)_2SO_4$ | 25 g |
| $MgSO_4 \cdot H_2O$ | 1 g |
| $FeSO_4 \cdot H_2O$ | 5 mg |
| $MnSO_4 \cdot H_2O$ | 5 mg |
| Yeast extract | 2 g |
| Calcium carbonate | 30 g |
| pH | 6.8 |

TABLE 5

| Strain | OD | sucrose consumption (g/L)* | L-threonine (g/L)** |
|---|---|---|---|
| KCCM10541 | 26.2 | 40.0 | 37.0 |
| KCCM10541 ΔysaA | 27.1 | 40.9 | 37.5 |
| KCCM10541 ΔdaS | 26.7 | 41.7 | 37.8 |
| KCCM10541 ΔybiX | 25 | 41.1 | 38.1 |
| KCCM10541 ΔysaA ΔydaS | 27.5 | 42.1 | 38.0 |
| KCCM10541 ΔdsS ΔybiX | 27.2 | 43.0 | 38.1 |
| KCCM10541 ΔybiX ΔysaA | 28.3 | 42.8 | 38.7 |
| KCCM10541 ΔysaA ΔydaS ΔybiX | 27.9 | 43.9 | 38.9 |

*measured at 24 hours
**measured at 48 hours

As can be seen in Table 5 above, we have demonstrated that the sucrose utilization of the recombinant L-threonine producing E. coli strains constructed according to the present invention increased by up to about 10% compared to that of the parent strain, and the production of threonine of the recombinant strains increased by up to about 5% compared to that in the parent strain. In view of the ATP level shown in FIG. 1, these results indicate that the activity and sucrose consumption rate or amino acid productivity of the recombinant strains were increased by the increased ATP level.

Example 6: Examination of Titer of L-Tryptophan Producing Strain, which has Attenuated Activity of Alone or a Combination of Enzymes that are Encoded by ysaA, ydaS and ybiX Gene, in Glucose-Containing Medium According to the methods described in Examples 1 and 2, alone or a combination of the ysaA, ydaS and ybiX genes was deleted from the L-tryptophan producing strain KCCM10812P (Korean Patent Registration No. 10-0792095) to increase the intracellular ATP level. The titers of the resulting strains were evaluated using glucose as a carbon source.

In order to examine the titer, the strains were inoculated by a platinum loop on LB solid medium and then cultured overnight in an incubator. And, it was inoculated by a platinum loop into 25 mL of flask titer medium having the composition shown in Table 6 below. Then, the strains were incubated in an incubator at 37 t and at 200 rpm for 48 hours. The results are shown in Table 7 below. All the results were recorded as the average of three flask results.

TABLE 6

| Composition | Concentration (per liter) |
|---|---|
| Glucose | 60 g |
| $K_2HPO_4$ | 1 g |
| $(NH_4)_2SO_4$ | 10 g |
| NaCl | 1 g |
| $MgSO_4 \cdot H_2O$ | 1 g |
| Sodium citrate | 5 g |
| Yeast extract | 2 g |
| Calcium carbonate | 40 g |
| Sodium citrate | 5 g |
| Phenylalanine | 0.15 g |
| Tyrosine | 0.1 g |
| PH | 6.8 |

TABLE 7

| Strain | OD | Glucose consumption (g/L)* | L-tryptophan (g/L)** |
|---|---|---|---|
| KCCM10812P | 18.2 | 47.2 | 5.7 |
| KCCM10812P ΔysaA | 18.3 | 48.3 | 6.9 |
| KCCM10812P ΔydaS | 18 | 49.1 | 6.6 |
| KCCM10812P ΔybiX | 17.7 | 50 | 6.0 |
| KCCM10812P ΔysaAΔydaS | 17.9 | 48.4 | 7.5 |
| KCCM10812P ΔydaSΔybiX | 18.7 | 49.3 | 7.6 |
| KCCM10812P ΔybiXΔysaA | 19.9 | 49 | 7.3 |
| KCCM10812P ΔysaAΔydaSΔybiX | 18.9 | 51.9 | 7.9 |

*measured at 33 hours
**measured at 48 hours

As can be seen in Table 7 above, we have demonstrated that the glucose consumption of the recombinant L-threonine producing E. coli strains constructed according to the present invention increased by up to about 10% compared to that of the parent strain, and the production of tryptophan of the recombinant strains increased by up to about 38% compared to that in the parent strain. In view of the ATP level shown in FIG. 2, these results indicate that the activity and glucose consumption rate or amino acid productivity of the recombinant strains were increased by the increased ATP level.

While the present invention has been described with reference to the particular illustrative embodiments, those skilled in the art to which the present invention pertains can understand that the present invention may be embodied in other specific forms without departing from the technical spirit or essential characteristics of the present invention. Therefore, the embodiments described above are considered to be illustrative in all respects and not restrictive. Furthermore, the scope of the present invention is defined by the appended claims rather than the detailed description, and it should be understood that all modifications or variations derived from the meanings and scope of the present invention and equivalents thereof are included in the scope of the appended claims.

Accession Number
Depository authority: Korean Culture Center of Microorganisms (International)
Accession Number: KCCM11243P
Deposition date: Dec. 29, 2011
Depository authority: Korean Culture Center of Microorganisms (International)
Accession Number: KCCM11245P
Deposition date: Dec. 29, 2011

The invention claimed is:

1. An L-threonine or L-tryptophan producing recombinant *Escherichia coli* strain, wherein the strain is modified by deletion of at least one polynucleotide, wherein the polynucleotide is selected from the group consisting of SEQ ID NO: 1, SEQ ID NO: 3, and SEQ ID NO: 5.

2. The L-threonine or L-tryptophan producing recombinant *Escherichia coli* strain according to claim 1, wherein the polynucleotide encodes a protein selected from the group consisting of YsaA having an amino acid sequence of SEQ ID NO: 2, a protein YdaS having an amino acid sequence of SEQ ID NO: 4, and a protein YbiX having an amino acid sequence of SEQ ID NO: 6.

3. The L-threonine or L-tryptophan producing recombinant *Escherichia coli* strain according to claim 1, wherein the recombinant *Escherichia coli* strain is L-threonine producing *Escherichia coli* CA03-4257P (KCCM11243P).

4. The L-threonine or L-tryptophan producing recombinant *Escherichia coli* strain according to claim 1, wherein the recombinant *Escherichia coli* strain is L-tryptophan producing *Escherichia coli* CA04-2002 (KCCM11245P).

5. A method for producing L-threonine or L-tryptophan, the method comprising culturing an L-threonine or L-tryptophan producing recombinant *Escherichia coli* strain, wherein the strain is modified by deletion of at least one polynucleotide, wherein the polynucleotide is selected from the group consisting of SEQ ID NO: 1, SEQ ID NO: 3, and SEQ ID NO: 5.

6. The method according to claim 5, wherein the recombinant *Escherichia coli* strain is L-threonine producing *Escherichia coli* CA03-4257P (KCCM11243P).

7. The method according to claim 5, wherein the recombinant *Escherichia coli* strain is L-tryptophan producing *Escherichia coli* CA04-2002 (KCCM11245P).

* * * * *

SEQUENCE LISTING

<160> NUMBER OF SEQ ID NOS: 24

<210> SEQ ID NO 1
<211> LENGTH: 474
<212> TYPE: DNA
<213> ORGANISM: Escherichia coli

<400> SEQUENCE: 1

```
atgaaccggt tattattgc ggatgcgacg aaatgtatcg gttgccgtac ctgtgaagtg      60
gcttgcgcag tgtcgcatca tgagaatcag gattgcgctg cgttgtcacc agacgagttt     120
atttcccgta ttcgtgtcat taaagaccac tgctggacca cggcagtagc ctgtcatcag    180
tgtgaagatg caccgtgcgc gaatgtctgc cctgttgacg cgataagccg cgaacatggg    240
catattttcg ttgaacaaac acgttgcatt ggctgtaaaa gctgtatgct ggcttgcccg    300
tttggtgcga tggaggtcgt ttcttcgcgc aaaaaggcga gggcgattaa gtgcgatctg    360
tgctggcatc gggagacggg accggcctgt gttgaagcct gcccgacaaa ggcgttgcag    420
tgcatggatg tcgagaaagt gcagcggcat cggctacggc agcagcctgt ttga          474
```

<210> SEQ ID NO 2
<211> LENGTH: 157
<212> TYPE: PRT
<213> ORGANISM: Escherichia coli

<400> SEQUENCE: 2

```
Met Asn Arg Phe Ile Ile Ala Asp Ala Thr Lys Cys Ile Gly Cys Arg
1               5                   10                  15

Thr Cys Glu Val Ala Cys Ala Val Ser His His Glu Asn Gln Asp Cys
                20                  25                  30

Ala Ala Leu Ser Pro Asp Glu Phe Ile Ser Arg Ile Arg Val Ile Lys
            35                  40                  45

Asp His Cys Trp Thr Thr Ala Val Ala Cys His Gln Cys Glu Asp Ala
        50                  55                  60

Pro Cys Ala Asn Val Cys Pro Val Asp Ala Ile Ser Arg Glu His Gly
65                  70                  75                  80

His Ile Phe Val Glu Gln Thr Arg Cys Ile Gly Cys Lys Ser Cys Met
                85                  90                  95

Leu Ala Cys Pro Phe Gly Ala Met Glu Val Val Ser Ser Arg Lys Lys
            100                 105                 110

Ala Arg Ala Ile Lys Cys Asp Leu Cys Trp His Arg Glu Thr Gly Pro
        115                 120                 125

Ala Cys Val Glu Ala Cys Pro Thr Lys Ala Leu Gln Cys Met Asp Val
    130                 135                 140

Glu Lys Val Gln Arg His Arg Leu Arg Gln Gln Pro Val
145                 150                 155
```

<210> SEQ ID NO 3
<211> LENGTH: 297
<212> TYPE: DNA
<213> ORGANISM: Escherichia coli

<400> SEQUENCE: 3

```
atgaaaaaag agaactattc attcaagcaa gcttgtgctg ttgtcggtgg gcaatcagca      60
atggctaggc ttttaggtgt atcacctcca agcgtaaatc aatggatcaa aggggtacgt     120
caattgcctg ccgagagatg tccagcaatt gaacgtgcaa caagaggtga ggttctgtgc     180
gaagaacttc gtcctgatat tgactggtca tatttacgac gttcggcatg ttgttcgcag     240
aatatgtcag tgaagcaact aaatgacagt aacaaatcct catttgatca tacctga       297
```

<210> SEQ ID NO 4
<211> LENGTH: 98
<212> TYPE: PRT
<213> ORGANISM: Escherichia coli

<400> SEQUENCE: 4

```
Met Lys Lys Glu Asn Tyr Ser Phe Lys Gln Ala Cys Ala Val Val Gly
1               5                   10                  15
Gly Gln Ser Ala Met Ala Arg Leu Leu Gly Val Ser Pro Pro Ser Val
            20                  25                  30
Asn Gln Trp Ile Lys Gly Val Arg Gln Leu Pro Ala Glu Arg Cys Pro
        35                  40                  45
Ala Ile Glu Arg Ala Thr Arg Gly Glu Val Leu Cys Glu Glu Leu Arg
    50                  55                  60
Pro Asp Ile Asp Trp Ser Tyr Leu Arg Arg Ser Ala Cys Cys Ser Gln
65                  70                  75                  80
Asn Met Ser Val Lys Gln Leu Asn Asp Ser Asn Lys Ser Ser Phe Asp
                85                  90                  95
His Thr
```

<210> SEQ ID NO 5
<211> LENGTH: 678
<212> TYPE: DNA
<213> ORGANISM: Escherichia coli

<400> SEQUENCE: 5

```
atgatgtacc acattcccgg cgtgttatcg ccacaggacg tcgctcgttt tcgcgaacaa      60
ctggaacaag ccgaatgggt ggatggacgc gtcaccaccg gcgcacaagg tgcgcaagtt     120
aagaacaatc aacaggtcga caccccgcagc acgttatacg ccgccctgca aaatgaggtg     180
ctgaacgcgg ttaaccaaca tgctttattc tttgccgcgg ccttgccgcg tacccttttcc     240
acgccgctgt ttaatcgcta tcagaacaat gaaacctatg gtttccatgt ggatggcgca     300
gtacgcagcc atccacaaaa cggctggatg cgtactgacc tttctgccac gctgtttta      360
agcgatccac aaagctacga cggcggcgaa ctggtcgtta atgacacctt cggacaacat     420
cgggtaaaac tcccggcagg cgatctcgtg ttgtatccct ccagcagcct gcattgcgtg     480
acacccgtaa cccgcggcgt acgagtggca tcatttatgt ggatccagtc gatgatccgc     540
gatgataaaa agcgcgccat gctgtttgaa ctggacaaca atattcagtc gctgaaaagc     600
cgctacggcg aaagtgaaga gatcctgtcg ctgcttaatc tttatcataa tctgctgcgg     660
gaatggtcgg agatctga                                                   678
```

<210> SEQ ID NO 6
<211> LENGTH: 225
<212> TYPE: PRT
<213> ORGANISM: Escherichia coli

<400> SEQUENCE: 6

Met Met Tyr His Ile Pro Gly Val Leu Ser Pro Gln Asp Val Ala Arg
1               5                   10                  15

Phe Arg Glu Gln Leu Glu Gln Ala Glu Trp Val Asp Gly Arg Val Thr
            20                  25                  30

Thr Gly Ala Gln Gly Ala Gln Val Lys Asn Asn Gln Val Asp Thr
        35                  40                  45

Arg Ser Thr Leu Tyr Ala Ala Leu Gln Asn Glu Val Leu Asn Ala Val
    50                  55                  60

Asn Gln His Ala Leu Phe Phe Ala Ala Ala Leu Pro Arg Thr Leu Ser
65                  70                  75                  80

Thr Pro Leu Phe Asn Arg Tyr Gln Asn Asn Glu Thr Tyr Gly Phe His
                85                  90                  95

Val Asp Gly Ala Val Arg Ser His Pro Gln Asn Gly Trp Met Arg Thr
            100                 105                 110

Asp Leu Ser Ala Thr Leu Phe Leu Ser Asp Pro Gln Ser Tyr Asp Gly
        115                 120                 125

Gly Glu Leu Val Val Asn Asp Thr Phe Gly Gln His Arg Val Lys Leu
    130                 135                 140

Pro Ala Gly Asp Leu Val Leu Tyr Pro Ser Ser Ser Leu His Cys Val
145                 150                 155                 160

Thr Pro Val Thr Arg Gly Val Arg Val Ala Ser Phe Met Trp Ile Gln
                165                 170                 175

Ser Met Ile Arg Asp Asp Lys Lys Arg Ala Met Leu Phe Glu Leu Asp
            180                 185                 190

Asn Asn Ile Gln Ser Leu Lys Ser Arg Tyr Gly Glu Ser Glu Glu Ile
        195                 200                 205

Leu Ser Leu Leu Asn Leu Tyr His Asn Leu Leu Arg Glu Trp Ser Glu
    210                 215                 220

Ile
225

<210> SEQ ID NO 7
<211> LENGTH: 70
<212> TYPE: DNA
<213> ORGANISM: Artificial Sequence
<220> FEATURE:
<223> OTHER INFORMATION: primer

<400> SEQUENCE: 7
gtagggacgc gctctctggc actctgctgt tttagtgcaa aggagtgatc aggtgacact    60
atagaacgcg                                                          70

<210> SEQ ID NO 8
<211> LENGTH: 70
<212> TYPE: DNA
<213> ORGANISM: Artificial Sequence
<220> FEATURE:
<223> OTHER INFORMATION: primer

<400> SEQUENCE: 8
ggcataaaca aagcgcactg ttccggcgtt gagaaacgcc ggaaaacgtt tagtggatct    60
gatgggtacc                                                          70

<210> SEQ ID NO 9
<211> LENGTH: 70
<212> TYPE: DNA

```
<213> ORGANISM: Artificial Sequence
<220> FEATURE:
<223> OTHER INFORMATION: primer

<400> SEQUENCE: 9
gctttggaca agtgccaaaa ctttaacatt tccttcgttg gatcaaagca gtagggacgc    60
gctctctggc                                                          70

<210> SEQ ID NO 10
<211> LENGTH: 70
<212> TYPE: DNA
<213> ORGANISM: Artificial Sequence
<220> FEATURE:
<223> OTHER INFORMATION: primer

<400> SEQUENCE: 10
attgaatttg gaagaatttg taggccggat aaggcgttta cgccgcatct ggcataaaca    60
aagcgcactg                                                          70

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
gagagaaaaa tctcctgaaa                                                20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
cctacatgat ttctgcaata                                                20

<210> SEQ ID NO 13
<211> LENGTH: 70
<212> TYPE: DNA
<213> ORGANISM: Artificial Sequence
<220> FEATURE:
<223> OTHER INFORMATION: primer

<400> SEQUENCE: 13
attgcgttag gcgtcgccta atatttctgt gtgttttttgg agttcattcg aggtgacact    60
atagaacgcg                                                          70

<210> SEQ ID NO 14
<211> LENGTH: 70
<212> TYPE: DNA
<213> ORGANISM: Artificial Sequence
<220> FEATURE:
<223> OTHER INFORMATION: primer

<400> SEQUENCE: 14
attcgatgtg ctcatgcttg attttcatga atcatttgcc tcttgatgtt tagtggatct    60
gatgggtacc                                                          70
```

```
<210> SEQ ID NO 15
<211> LENGTH: 70
<212> TYPE: DNA
<213> ORGANISM: Artificial Sequence
<220> FEATURE:
<223> OTHER INFORMATION: primer

<400> SEQUENCE: 15
ttacattagg caatccctac ccttactgca ttaggcacag cctattgaca attgcgttag      60
gcgtcgccta                                                             70

<210> SEQ ID NO 16
<211> LENGTH: 70
<212> TYPE: DNA
<213> ORGANISM: Artificial Sequence
<220> FEATURE:
<223> OTHER INFORMATION: primer

<400> SEQUENCE: 16
attggctacc catgcctgcc cttttcggc tgctagggca acaacactg attcgatgtg        60 ctcatgcttg                                                             70

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tatagagcct ttcttaatcc                                                  20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
cgcagatatt cttcagtaat                                                  20

<210> SEQ ID NO 19
<211> LENGTH: 70
<212> TYPE: DNA
<213> ORGANISM: Artificial Sequence
<220> FEATURE:
<223> OTHER INFORMATION: primer

<400> SEQUENCE: 19
catttctgat tcagatgtgg ggcgcaggcc ccacttttg gagaaattgt aggtgacact        60
atagaacgcg                                                             70

<210> SEQ ID NO 20
<211> LENGTH: 70
<212> TYPE: DNA
<213> ORGANISM: Artificial Sequence
<220> FEATURE:
<223> OTHER INFORMATION: primer

<400> SEQUENCE: 20
tgtacagtta agtgtagcta atccagggac gaactcgggc agttcaagca tagtggatct      60
gatgggtacc                                                             70
```

```
<210> SEQ ID NO 21
<211> LENGTH: 70
<212> TYPE: DNA
<213> ORGANISM: Artificial Sequence
<220> FEATURE:
<223> OTHER INFORMATION: primer

<400> SEQUENCE: 21
accgttatca cccgggcgag ccaagaacct tcttgctcac agccaatatg catttctgat      60
tcagatgtgg                                                            70

<210> SEQ ID NO 22
<211> LENGTH: 70
<212> TYPE: DNA
<213> ORGANISM: Artificial Sequence
<220> FEATURE:
<223> OTHER INFORMATION: primer

<400> SEQUENCE: 22
gtcatcgtta gcccaaccgg atgccatatc gacctcccca tatcaatact tgtacagtta     60
agtgtagcta                                                            70

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
aaaggttcag acggcgcggt                                                 20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
taagcgcacg ccaggaatgg                                                 20
```